United States Patent [19]

Nakai et al.

[11] Patent Number: 4,497,957

[45] Date of Patent: Feb. 5, 1985

[54] PROCESS FOR PREPARING OPTICALLY ACTIVE TRYPTOPHANS

[75] Inventors: Mamoru Nakai; Tokio Ohshima; Tomio Kimura; Tetsuo Omata; Noritada Iwamoto, all of Ube, Japan

[73] Assignee: Ube Industries, Ltd., Yamaguchi, Japan

[21] Appl. No.: 391,997

[22] Filed: Jun. 25, 1982

Related U.S. Application Data

[63] Continuation-in-part of Ser. No. 276,057, Jun. 22, 1981, abandoned.

[30] Foreign Application Priority Data

Jun. 24, 1980 [JP] Japan ................................ 55-84618

[51] Int. Cl.³ ........................................... C07D 209/20
[52] U.S. Cl. .................................................. 548/496
[58] Field of Search ......................................... 548/496

[56] References Cited

FOREIGN PATENT DOCUMENTS 4010146 3/1958 Japan ................................ 548/496
4015541 8/1967 Japan ................................ 548/496

OTHER PUBLICATIONS

March Index, 9th Ed, (1976), Item 8815, p. 1171.
Chibata et al, Bull Ag. Chem Soc. Japan, vol. 21, No. 1, pp. 62–66 (1957).

*Primary Examiner*—Glennon H. Hollrah
*Assistant Examiner*—D. B. Springer
*Attorney, Agent, or Firm*—Austin R. Miller

[57] ABSTRACT

Biochemical optical resolution of DL-tryptophans in which DL-tryptophan amides are interacted with the culture products, or their treated products, of a microorganism capable of producing amidase is described. L-Tryptophan amides in racemic DL-tryptophan amides are asymmetrically hydrolyzed to form optically active L-tryptophans at a high yield and almost all D-tryptophan amides remain without being subjected to hydrolysis. The resultant D-tryptophan amides are readily hydrolyzed, after separating L-tryptophans, to form optically active D-tryptophans at a high yield.

11 Claims, No Drawings

PROCESS FOR PREPARING OPTICALLY ACTIVE TRYPTOPHANS

CROSS-REFERENCES TO RELATED APPLICATION

This application is a continuation-in-part of Ser. No. 276,057, filed June 22, 1981, now abandoned.

BACKGROUND OF THE INVENTION

1. Field of the Invention

The present invention relates to a process for preparing optical active tryptophans by biochemical asymmetric hydrolysis of DL-tryptophan amides, in which an amidase derived from a microorganism is utilized.

2. Description of the Prior Art

It is well-known in the art that L-tryptophans and D-tryptophans are optically active and have different properties and uses. For instance, L-tryptophan is an important compound as an essential amino acid and is suitable for use in an amino acid infusion solution, an animal food stuff additive, hypnotizing agent and the like. On the other hand, D-tryptophan is useful as, for example, a dentifrice additive and a sweetening agent.

Many organic synthesis methods for preparing tryptophans have been heretofore proposed. However, when the tryptophans are prepared by organic synthesis methods, the products are obtained in the form of mixtures of D-tryptophans and L-tryptophans, i.e. racemic mixtures. Therefore, the effective optical resolution of DL-tryptophans is an extremely important problem to be solved in the art.

Proposed optical resolution methods of DL-tryptophans are only those in which hydantoin or N-acyl derivatives of DL-tryptophans are used as a substrate and in which microorganisms capable of producing hydantoinase or acylase are interacted with the substrate. Thus, the development of the substrate and the microorganisms used in the field of the biochemical optical resolution of DL-tryptophans are extremely limited.

SUMMARY OF THE INVENTION

Accordingly, an object of the present invention is to obviate the afore-mentioned problems in the prior arts and to provide a novel biochemical optical resolution of DL-tryptophans in which L-tryptophans and D-tryptophans can be separated from each other at a high yield.

Another object of the present invention is to selectively hydrolyze L-tryptophan amides, whereby optical active L-tryptophans are prepared at a high yield.

A further object of the present invention is to hydrolyze D-tryptophan amides after the separation of L-tryptophans from DL-tryptophan amides, whereby optical active D-tryptophans are prepared at a high yield.

Other objects and advantages of the present invention will be apparent from the description set forth hereinbelow.

In accordance with the present invention, there is provided a process for preparing optically active L-tryptophans having a general formula:

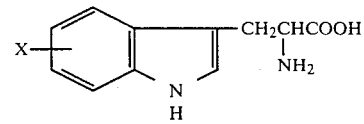

wherein X represents hydrogen, hydroxyl group, halogen atoms such as fluorine, chlorine, bromine and iodine, lower alkyl groups, preferably having 1 to 4 carbon atoms, or lower alkoxy groups, preferably having 1 to 4 carbon atoms, comprising the steps of:

(a) interacting DL-tryptophan amides having a general formula:

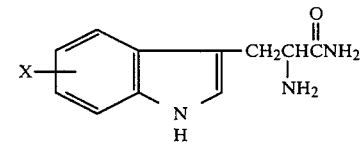

wherein X is as defined above with (i) a cultivation mixture of a microorganism capable of producing amidase, (ii) a culture broth or cells separated from the cultivation mixture, (iii) the amidase isolated from the culture broth or cells, or (iv) immobilized preparations of the cultivation mixture, the culture broth or cells, or the amidase, said microorganism being selected from the group of genera Trichoderma, Rhodotorula, Nocardia, Mycobacterium, Bacillus, Rhizopus, Candida, Streptomyces, Aerobacter, Pseudomonas, Gibberella, Torulopsis, Enterobacter, and Trichosporon, whereby the asymmetric hydrolysis of L-tryptophan amides is effected; and (b) separating the resultant L-tryptophans from the asymmetrically hydrolyzed mixture.

In accordance with the present invention, there is also provided a process for preparing optically active D-tryptophans having a general formula

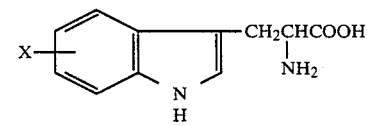

wherein X is as defined above, comprising the steps of:

(a) interacting DL-tryptophan amides having a general formula,

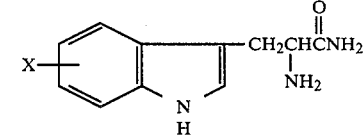

wherein X is as defined above with (i) a cultivation mixture of a microorganism capable of producing amidase, (ii) a culture broth or cells separated from the cultivation mixture, (iii) the amidase isolated from the culture broth or cells, or (iv) immobilized preparations of the cultivation mixture, the culture broth or cells, or the amidase, said microorganism being selected from the group of genera Trichoderma, Rhodotorula, Nocardia, Mycobacterium, Bacillus, Rhizopus, Candida, Streptomyces, Aerobacter, Pseudomonas, Gibberella, Torulopsis, Enterobacter, and Trichosporon, whereby the asymmetric hydrolysis of L-tryptophan amides is effected;

(b) separating the resultant L-tryptophans obtained from the asymmetric hydrolysis of L-tryptophan amides, and;

(c) hydrolyzing the resultant D-tryptophan amides.

DETAILED DESCRIPTION OF THE INVENTION

Biochemical asymmetric hydrolysis of DL-tryptophan amides in which an enzyme derived from animal visceral organs is employed is reported [see: Bull. Agr. Chem. Soc. Japan, Vol. 21, No. 1, P. 62-66 (1957)]. However, the biochemical asymmetric hydrolysis of DL-tryptophan amides in which there is employed an enzyme derived from microorganisms has not been reported.

According to the present invention, new substrates are provided in the biochemical optical resolution of DL-tryptophans in which an enzyme derived from microorganisms is employed and the variety of the microorganisms which can be utilized in the optical resolution is widened. Thus, the present invention is industrially very valuable in this field.

The DL-tryptophan amides employed as a substrate in the practice of the present invention can be readily synthesized by, for example, reacting the esters of DL-tryptophans with ammonia in a conventional manner.

The microorganisms which can produce the amidase used in the practice of the present invention are those which belong to any systematic group, so long as they have the capability of selectively hydrolyzing only L-tryptophan amides in the racemic mixture of DL-tryptophan amides. Examples of the genus names of these microorganisms are listed in the following Table, in which the typical species name of the microorganism belonging to each genus is also listed. However it should be noted that the microorganisms which can be employed in the practice of the present invention are not limited to these specific examples. All the exemplified microorganisms are known and also readily available from the depository of IFO (Institute for Fermentation, Osaka, Japan).

TABLE

| | NAME OF MICROORGANISMS | DEPOSIT NO. |
|---|---|---|
| (1) | Genus Rhizopus<br>*Rhizopus chinensis* | IFO-4768 |
| (2) | Genus Gibberella<br>*Gibberella fujikuroi* | IFO-5268 |
| (3) | Genus Trichoderma<br>*Trichoderma viride* | IFO-4847 |
| (4) | Genus Torulopsis<br>*Torulopsis candida* | IFO-0768 |
| (5) | Genus Candida<br>*Candida utilis* | IFO-0396 |
| (6) | Genus Trichosporon<br>*Trichosporon cutaneum* | IFO-0173 |
| (7) | Genus Mycobacterium<br>*Mycobacterium phlei* | IFO-3158 |
| (8) | Genus Nocardia<br>*Nocardia asteroides* | IFO-3424 |
| (9) | Genus Streptomyces<br>*Streptomyces griseus* | IFO-3356 |
| (10) | Genus Enterobacter<br>*Enterobacter cloacae* | IFO-3320 |
| (11) | Genus Bacillus<br>*Bacillus subtilis* | IFO-3026 |
| (12) | Genus Pseudomonas<br>*Pseudomonas fluorescens* | IFO-3081 |
| (13) | Genus Aerobacter<br>*Aerobacter aerogenes* | IFO-3317 |
| (14) | Genus Rhodotorula<br>*Rhodotorula glutinis* var. rubescenes | IFO-0413 |

In the practice of the present invention, the above mentioned microorganisms can be interacted with the DL-tryptophan amides in the form of (i) cultivation mixtures of the above-mentioned microorganisms, (ii) culture brothes or cells separated from the cultivation mixtures, (iii) the enzyme (i.e. amidase) isolated from the culture brothes or cells according to any conventional enzyme isolating technique (e.g. the crude enzyme, the purified enzyme, the enzyme-containing extracts or the concentrated solutions thereof), or (iv) immobilized preparations of the cultivation mixtures, the culture brothes or cells or amidase, on various carriers.

Examples of the carriers are natural products such as alginic acid, carrageenan, collagen, cellulose, acetylcellulose, agar-agar, cellophane, collodion and the like, and synthetic polymer substances such as polyacrylamide, polystyrene, polyethylene glycol, polypropylene glycol, polyurethane, polybutadiene and the like. The immobilization of the cells or enzymes on the carrier can be carried out in the conventional manner under moderate conditions so that the activity of amidase is not impaired.

The suitable reaction temperature of the asymmetric hydrolysis according to the present invention can be within the range of from 20° to 50° C. However, in order to minimize the decrease in the enzymatic activity, the use of the reaction temperature of from 25° to 40° C. is economically advantageous.

The suitable reaction time of the asymmetric hydrolysis according to the present invention can be within the range of from 5 to 50 hours. However, the reaction time can be shortened by raising the reaction temperature or by increasing the amount of the enzymes used. Furthermore, the reaction can be generally carried out at a pH of 5 through 10, more preferably 7 through 9.

The amount of the microorganisms employed in the practice of the present invention is preferably in a weight ratio of from 0.01 to 2, in terms of the freeze dried cells, based on the weight of the DL-tryptophan amides. In the case where the cultivation mixtures of the microorganisms, treated products thereof, or the immobilized products thereof are employed, the amount thereof can be determined in terms of the amount of the freeze dried cells. The suitable concentration of the substrate, i.e. DL-trypotophan amides in the reaction mixture is generally within the range of from 1 to 40% by weight, more preferably 5 to 30% by weight.

According to the present invention, the asymmetric hydrolysis reaction is stopped after the hydrolysis of L-tryptophan amides proceeds at the conversion rate of almost 100%, and, then, L-tryptophans and D-tryptophan amides are separately isolated from the reaction mixture. This separation can be readily carried out by using any conventional separation techniques, such as fractional crystallization and solvent extraction.

D-tryptophan amides are not affected by the action of the microorganisms in the above mentioned asymmetric hydrolysis and, therefore, almost all D-tryptophan amides can be recovered from the racemic mixture. The D-tryptophan amides thus recovered can be readily hydrolyzed by using any conventional technique, for example, by heating in the presence of an aqueous acid or alkaline solution. Thus, optically active D-tryptophans can be obtained at a high yield. The D-tryptophan amides recovered above can also be subjected to a racemization and reused as a substrate in the asymmetric hydrolysis of the present invention.

The optical purity and yield of the L-tryptophans as well as the D-tryptophans are equal to or more than those obtained from known biochemical optical resolution.

The L-tryptophans separated according present invention can be advantageously used as hypnotizing agents, animal food stuff additives and amino acid infusion solutions. Furthermore, the D-tryptophans separated according to the present invention can be advantageously used as sweetening agents.

EXAMPLES

The present invention will now be further illustrated by, but is by no means limited to, the following Examples wherein the yield of L- or D-tryptophans is calculated from the following equation.

$$\text{Yield (\%)} = \frac{\text{moles of the resultant L- or D-tryptophans}}{\text{moles of the L- or D-tryptophan amides in the starting substrate}} \times 100$$

EXAMPLES 1 THROUGH 14

Synthesis of DL-tryptophan amide 50 g of DL-tryptophan available from Nakarai Chemicals, Kyoto, Japan, was suspended in 500 ml of methanol and 40 ml of thionyl chloride was dropwise added thereto while vigorously stirring. The reaction was exothermic and the reaction mixture was allowed to be refluxed for 10 hours while stirring. Then, the solvent was distilled off and the resultant residue was washed with diethylether. Thus, DL-tryptophan methylester hydrochloride was obtained in the form of white crystals.

The tryptophan methylester hydrochloride thus obtained was suspended in 1 liter of ethyl acetate and 100 ml of triethylamine was added thereto. The mixture was allowed to react for 1 hour while vigorously stirring. The insoluble matter (i.e. triethylamine hydrochloride) was filtered off and the filtrate was washed with a small amount of water. Thereafter, the solvent was distilled off to obtain 40 g of oily tryptophan methylester.

The resultant oily product was charged into a stainless steel autoclave and 50 g of liquid ammonia was added thereto. The mixture was allowed to react at a temperature of 50° C. for 10 hours. The remaining ammonia and the formed methanol were distilled off. Thus, 35 g of DL-tryptophan amide was obtained in the form of white crystals. The yield of the isolated DL-tryptophan amide based on the starting tryptophan was 70%. The melting point of the product after recrystallization from water was 127° to 129° C.

The resultant DL-tryptophan amide thus obtained was used in the following examples.

Biochemical Asymmetric Hydrolysis of DL-Tryptophan Amide 100 ml of a culture medium having a pH of 7.0 and containing 5% by weight of glycerol, 5% by weight of corn steep liquor, 0.5 % by weight of ammonium sulfate and 1 ml of a mixture of inorganic salts was charged into a shaking flask. The inorganic salt mixture was prepared by dissolving 20 g of $MgSO_4.7H_2O$, 5 g of $FeSO_4.7H_2O$, 2 g of $CaCl_2$, 0.2 g of $MnCl_2.4H_2O$, 0.1 g of $NaMoO_4.2H_2O$ and 0.1 g of NaCl in 1000 ml of distilled water. After sterilizing the content of the flask, 2 loopfuls of each of the microorganisms listed in Table 1 below were inoculated from an agar slant and, then, the reciprocal shaking culture (or incubation) was carried out at a temperature of 30° C. for 65 hours.

Thereafter, 2 g of DL-tryptophan amide prepared above was added to the flask and, then, the reciprocal shaking culture was carried out for 48 hours at a temperature of 30° C. The cells were removed from the reaction mixture by centrifugation or filtration. The pH of the culture filtrate was adjusted to 6.0 and, then, the filtrate was vacuum concentrated until the volume of the filtrate became 5 through 10 ml. The crystallized L-tryptophan was collected by filtration after cooling.

The results are shown in the following Table 1.

TABLE 1

| Example No. | Microorganism as used | | Formed L-Tryptophan Isolation Yield (%) | Optical Rotation $[\alpha]_D^{20}$ (C = 0.5, $H_2O$) |
|---|---|---|---|---|
| 1 | Aerobacter aerogenes | IFO-3317 | 52 | −31.5° |
| 2 | Bacillus subtilis | IFO-3026 | 47 | −30.5° |
| 3 | Candida utilis | IFO-0396 | 44 | −31.2° |
| 4 | Rhodotorula glutinis var. rubescens | IFO-0413 | 54 | −33.0° |
| 5 | Rhizopus chinensis | IFO-4768 | 51 | −32.0° |
| 6 | Trichoderma viride | IFO-4847 | 27 | −30.0° |
| 7 | Nocardia asteroides | IFO-3424 | 29 | −29.8° |
| 8 | Mycobacterium phlei | IFO-3158 | 25 | −31.0° |
| 9 | Streptomyces griseus | IFO-3356 | 30 | −29.5° |
| 10 | Enterobacter cloacae | IFO-3320 | 32 | −30.0° |
| 11 | Pseudomonas flurescens | IFO-3081 | 28 | −32.0° |
| 12 | Gibberella fujikuroi | IFO-5268 | 31 | −29.5° |
| 13 | Torulopsis candida | IFO-0768 | 23 | −29.8° |
| 14 | Trichosporon cutaneum | IFO-0173 | 26 | −33.0° |

EXAMPLE 15

From the cultivation mixture of Rhodotorula glutinis var. rubescens prepared in a manner as described in Example 4, the cells were collected by centrifugation and, then, washed twice with distilled water.

The washed cells were added to 100 ml of a 0.1M phosphate buffer solution having a pH of 7.0 and containing 2 g of DL-tryptophan amide and the mixture was incubated for 20 hours at a temperature of 30° C.

After the completion of the reaction, the cells were removed from the reaction mixture by centrifugation.

The reaction mixture thus obtained was analyzed by high speed liquid chromatography. The resultant reaction mixture contained 983 mg of L-tryptophan (yield: 98%) and 1010 mg of D-tryptophan amide. From this reaction mixture the unreacted D-tryptophan amide was extracted with ethyl acetate.

On the other hand, the pH of the water layer after the extraction was adjusted to 5.9 by using 2N sulfuric acid. Then, the resultant solution was vacuum concentrated until the total volume of the solution became about 20 ml. After ice-cooling, 330 mg of the crystallized L-tryptophan having a melting point of 280°–282° C. (decomposition) and $[\alpha]_D^{20}$ of $-33.5°$ (C=0.5 H$_2$O) was collected.

EXAMPLE 16

The washed cells of *Rhodotorula glutinis* var. *rubescens* prepared in a manner as described in Example 15 were washed with cold acetone. Thus, acetone dried cells were obtained.

On the other hand, DL-tryptophan amide was dissolved in distilled water and substrate solutions having various concentrations listed in Table 2 below and having a pH of 7.0 were prepared.

The above mentioned acetone dried cells were added to 10 ml of the substrate solution in such an amount that a weight ratio of the dried cells to the substrate were 0.2. Then, the reaction was carried out at a temperature of 30° C. for 20 hours. The resultant reaction mixture was analyzed to determined the yield of L-tryptophan by using high speed liquid chromatography.

The results are shown in Table 2 below.

TABLE 2

| Concentration of Substrate (i.e. DL-tryptophan Amide) | Yield (%) of L-Tryptophan |
| --- | --- |
| 1 | 100 |
| 2 | 100 |
| 5 | 100 |
| 10 | 100 |
| 20 | 92 |
| 30 | 75 |
| 40 | 55 |

EXAMPLE 17

The washed cells of *Rhodotorula glutinis* var. *rubescens* prepared in a manner as described in Example 15 were freeze dried.

The freeze dried cells were added to 10 ml of distilled water containing 10% by weight of DL-tryptophan amide (pH=7.5) in the weight ratio of the cells to the substrate listed in Table 3 below. Then, mixture was incubated at a temperature of 30° C. for 20 hours.

The reaction mixture was analyzed to determine the yield of L-tryptophan by high speed liquid chromatography.

The results are shown in Table 3 below.

TABLE 3

| Freeze Dried Substrate Cells (weight ratio) | Yield (%) of L-Tryptophan |
| --- | --- |
| 0.01 | 73 |
| 0.05 | 98 |
| 0.1 | 100 |
| 0.5 | 100 |
| 1.0 | 100 |

EXAMPLE 18

50 mg of the freeze dried cells of *Rhodotorula glutinis* var. *rubescens* prepared in a manner as described in Example 17 were suspended in 5 ml of 0.2M phosphate buffer solution and, then, the cells were disrupted under cooling by using a French press (20,000 psi). The resultant mixture was centrifuged under 20,000×g for 30 mins. To 5 ml of the supernatant solution thus obtained, 250 mg of DL-tryptophan amide was added and the pH of the mixture was adjusted to 7.5. Thereafter, the mixture was incubated at a temperature of 30° C. for 20 hours.

The reaction mixture was analyzed by a high speed liquid chromatography. L-Tryptophan was obtained at a yield of 95%.

EXAMPLE 19

To 5 ml of the cell-free extract of *Rhodotorula glutinis* var. *rubescens* prepared in a manner as described in Example 18, ammonium sulfate was added. The protein which was precipitated at a saturation of 25 to 75% was collected by centrifugation. Then, 5 ml of 0.2M phosphate buffer solution containing 250 mg of DL-tryptophan amide and having a pH of 7.5 was added thereto and the mixture was incubated at a temperature of 30° C. for 20 hours.

The reaction mixture was analyzed by high speed liquid chromatography. L-Tryptophan was obtained at a yield of 63%.

EXAMPLE 20

10 ml of the cell-free extract of *Rhodotorula glutinis* var. *rubescens* prepared in a manner as described in Example 18 was passed through the column having a diameter of 1.5 cm and a length of 65 cm and packed with Sephadex G-75 and fractions having the amidase activity were collected. These fractions were concentrated by using a semipermeable membrane method to a volume of 5 ml. Then, 250 mg of DL-tryptophan amide was added thereto and the mixture was incubated at a temperature of 30° C. for 20 hours.

The reaction mixture was analyzed by high speed liquid chromatography. L-Tryptophan was obtained at a yield of 56%.

EXAMPLE 21

The washed cells (corresponding to 1.0 g of the freeze dried cells) of *Rhodotorula glutinis* var. *rubescens* prepared in a manner as described in Example 15 were suspended in 15 ml of 0.1M phosphate buffer solution having a pH of 7.0 and, then, 3.75 g of acrylamide monomer, 0.2 g of N,N'-methylene bisacrylamide (i.e. crosslinking agent), 2.5 ml of a 5% aqueous 3-dimethylamino propionitrile solution (i.e. polymerization promotor) and 2.5 ml of 2.5% aqueous potassium persulfate solution (i.e. polymerization initiator) were added and mixed with one another. The mixture was allowed to stand at a temperature of 25° C. for 1 hour, whereby the gellation of the mixture was complete.

The gel thus obtained was crushed and washed with water. The resultant immobilized product, (i.e., gel particles, having a particle diameter of 0.2 to 0.5 mm) was packed into a column having a diameter of 2 cm and a length of 50 cm. Thereafter, distilled water containing 10% by weight of DL-tryptophan amide and having a pH of 7.5 was passed through the column at a temperature of 30° C. from the top of the column at a space velocity (SV) of 0.2.

In this continuous reaction, the yield of the L-tryptophan was maintained at a yield of 80% or more until the reaction time became 200 hours.

EXAMPLE 22

Example 4 was repeated except that 2.0 g of DL-5-hydroxytryptophan amide was used as a substrate. The DL-5-hydroxytryptophan amide was prepared in the same manner as described in Examples 1 through 14 except that DL-5-hydroxytryptophan was used as a starting material.

As a result, L-5-hydroxytryptophan was obtained at a yield of 43%.

EXAMPLE 23

Example 14 was repeated except that 2.0 g of DL-6-methoxytryptophan amide was used as a substrate. The DL-6-methoxytryptophan amide was prepared in the same manner as described in Examples 1 through 14 except that DL-6-methoxytryptophan was used as a starting material.

As a result, L-6-methoxytryptophan was obtained at a yield of 27%.

EXAMPLE 24

Example 1 was repeated except that Candida kurusei (IFO-0013) was used as microorganism and DL-5-methyltryptophan amide was used as a substrate. The DL-5-methyltryptophan amide was prepared in the same manner as described in Examples 1 through 14 except that DL-5-methyltryptophan was used as a starting material.

As a result, L-5-methyltryptophan was obtained at a yield of 23%.

EXAMPLE 25

Example 4 was repeated except that 2.0 g of DL-6-chlorotryptophan amide was used as a substrate. The DL-6-chlorotryptophan amide was prepared in the same manner as described in Examples 1 through 14 except that DL-6-chlorotryptophan was used as a starting material.

As a result, L-6-chlorotryptophan was obtained at a yield of 34%.

EXAMPLE 26

To 500 mg of D-tryptophan amide recovered in the manner as described in Example 15, 5 ml of concentrated hydrochloric acid was added and, then, the mixture was heated at a temperature of 90° C. for 3 hours, whereby the hydrolysis reaction was effected. After the completion of the reaction, concentrated hydrochloric acid was vacuum distilled off. 5 ml of water was added to the residue and the pH thereof was adjusted to 6.0. After ice cooling, 460 mg of the precipitated D-tryptophan having $[\alpha]_D^{20}$ of +33.3° (C=0.5 H$_2$O) was collected by filtration. The yield of the isolated D-tryptophan was 92%.

We claim:

1. A process for preparing optically active L-tryptophans having the formula,

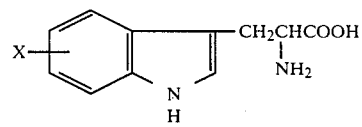

wherein X represents hydrogen, hydroxyl group, halogen atoms, lower alkyl groups or lower alkoxy groups comprising the steps of:

(a) interacting DL-tryptophan amides having the formula,

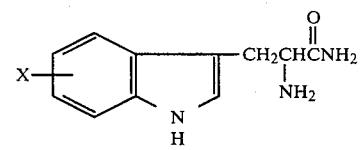

wherein X is as defined above with (i) a cultivation mixture of a microorganism capable of producing amidase, (ii) a culture broth or cells separated from the cultivation mixture, (iii) the amidase isolated from the culture broth or cells, or (iv) immobilized preparations of the cultivation mixture, the culture broth or cells, or the amidase, said microorganism being selected from the group of genera Trichoderma, Rhodotorula, Nocardia, Mycobacterium, Bacillus, Rhizopus, Candida, Streptomyces, Aerobacter, Pseudomonas, Gibberella, Torulopsis, Enterobacter, and Trichosporon, whereby the asymmetric hydrolysis of L-tryptophan amides is effected; and (b) separating the resultant L-tryptophanes from the asymmetrically hydrolyzed mixture.

2. A process as claimed in claim 1, wherein the reaction temperature of the asymmetric hydrolysis of L-tryptophan amides is within the range of from 20° to 50° C.

3. A process as claimed in claim 1, wherein the reaction time of the asymmetric hydrolysis of L-tryptophan amides is within the range of from 5 to 50 hours.

4. The process as claimed in claim 1, wherein the amount of the microorganism is in a weight ratio of from 0.01 to 2, in terms of freeze dried cells of the microorganism, based on the weight of the DL-tryptophan amides.

5. A process for preparing optically active D-tryptophans having the formula,

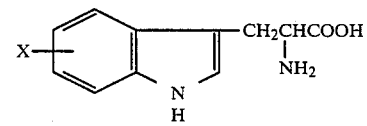

wherein X represents hydrogen, hydroxyl group, halogen atoms, lower alkyl groups or lower alkoxy groups comprising the steps of:

(a) interacting DL-tryptophan amides having the formula,

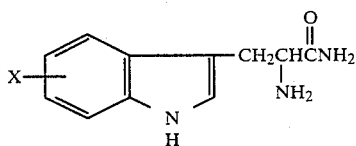

wherein X is as defined above with (i) a cultivation mixture of a microorganism capable of producing amidase, (ii) a culture broth or cells separated from the cultivation mixture, (iii) the amidase isolated from the culture broth or cells, or (iv) immobilized preparations of the cultivation mixture, the culture broth or cells, or the amidase, said microorganism being selected from the group of genera Trichoderma, Rhodotorula, Nocardia, Mycobacterium, Bacillus, Rhizopus, Candida, Streptomyces, Aerobacter, Pseudomonas, Gibberella, Torulopsis, Enterobacter, and Trichosporon, whereby the asymmetric hydrolysis of L-tryptophan amides is effected;

(b) separating the resultant L-tryptophans obtained from the asymmetric hydrolysis of L-tryptophan amides, and;

(c) hydrolyzing the resultant D-tryptophan amides.

6. A process as claimed in claim 5, wherein the reaction temperature of the asymmetric hydrolysis of L-tryptophan amides is within the range of from 20° to 50° C.

7. A process as claimed in claim 5, wherein the reaction time of the asymmetric hydrolysis of L-tryptophan amides is within the range of from 5 to 50 hours.

8. A process as claimed in claim 5, wherein the amount of the microorganism is in a weight ratio of from 0.01 to 2, in terms of freeze dried cells of the microorganism based, on the weight of the DL-tryptophan amides.

9. A process as claimed in claim 5, wherein the hydrolysis of the D-tryptophan amides is carried out in the presense of an aqueous acid or alkaline solution.

10. A process as claimed in claim 1, wherein said microorganisms are selected from the group consisting of *Rhizopus chinensis, Gibberella fujikuroi, Trichoderma viride, Torulopsis candida, Candida utilis, Trichosporon cutaneum, Mycobacterium phlei, Nocardia asteroides, Streptomyces griseus, Enterobacter cloacae, Bacillus subtilis, Pseudomonas fluorescens, Aerobacter aerogenes* and *Rhodotorula glutinis* var. *rubescense.*

11. A process as claimed in claim 5, wherein said microorganisms are selected from the group consisting of *Rhizopus chinensis, Gibberella fujikuroi, Trichoderma viride, Torulopsis candida, Candida utilis, Trichosporon cutaneum, Mycobacterium phlei, Nocardia asteroides, Streptomyces griseus, Enterobacter cloacae, Bacillus subtilis, Pseudomonas fluorescens, Aerobacter aerogenes* and *Rhodotorula glutinis* var. *rubescenes.*

* * * * *